United States Patent [19]

Franko-Filipasic et al.

[11] Patent Number: 4,851,587
[45] Date of Patent: Jul. 25, 1989

[54] SINGLE SOLVENT PROCESS FOR PREPARING 2-METHALLYLOXY-PHENOL FROM CATECHOL

[75] Inventors: Borivoj Franko-Filipasic, Morrisville, Pa.; James Snyder, Yardville, N.J.

[73] Assignee: FMC Corporation, Philadelphia, Pa.

[21] Appl. No.: 200,336

[22] Filed: May 31, 1988

[51] Int. Cl.$^4$ .............................................. C07C 41/16
[52] U.S. Cl. .................................. 568/652; 568/766; 549/462
[58] Field of Search ................. 568/652, 766; 549/462

[56] References Cited

U.S. PATENT DOCUMENTS

| | | | |
|---|---|---|---|
| 3,474,170 | 10/1969 | Scharpf | 424/285 |
| 3,474,171 | 10/1969 | Scharpf | 424/285 |
| 4,250,333 | 2/1981 | Rakoutz | 568/652 |
| 4,321,204 | 3/1982 | Buttner et al. | 260/346.22 |
| 4,618,728 | 10/1986 | Hobson et al. | 568/652 |

FOREIGN PATENT DOCUMENTS 0092102 10/1983 European Pat. Off. .
173437 8/1979 Hungary .

*Primary Examiner*—Bruce D. Gray
*Attorney, Agent, or Firm*—Patrick C. Baker; H. Robinson Ertelt

[57] ABSTRACT

2-Methallyloxyphenol precursor to 2,3-dihydro-2,2-dimethyl-7-hydroxybenzofuran is prepared selectively and in good yield in the etherification of an alkali metal catecholate by methallyl chloride in an improved process using the same solvent medium for both the precursor and the hydroxybenzofuran, the process characterized by a solvent medium comprising an aromatic hydrocarbon solvent, the medium also containing an amine selected from alkylamines and N-heterocyclic amines. The amine forms a quaternary salt with the methallyl chloride in situ to catalyze the etherification and the aromatic solvent permits rearrangement of the product and Claisen closure to a benzofuran intermediate without solvent exchange.

11 Claims, No Drawings

SINGLE SOLVENT PROCESS FOR PREPARING 2-METHALLYLOXY-PHENOL FROM CATECHOL

TECHNICAL FIELD

This invention relates to the preparation of 2-methallyloxyphenol by the selective monoetherification of catechol.

BACKGROUND OF THE INVENTION

2-Methallyloxyphenol is a known intermediate for the synthesis of benzofuranyl insecticides, as disclosed in U.S. Pat. No. 3,474,170. In one process for producing 2-methallyloxyphenol by the reaction of methallyl chloride with catechol (also known as "pyrocatechol") as described in U.S. Pat. No. 3,474,171 and Hungarian Pat. No. 173,437, the reaction is conducted in an aliphatic ketone such as acetone or methyl ethyl ketone in the presence of a base as an acid acceptor and a catalyst such as potassium iodide. U.S. Pat. Nos. 4,250,333 and 4,618,728 describe various conditions for improving this reaction, including selection of solvent and base.

2-Methallyloxyphenol can undergo a Claisen rearrangement and subsequent ring closure in a known manner to form 2,3-dihydro-2,2-dimethyl-7-hydroxybenzofuran, a precursor to carbofuran. Both of these reactions are conducted in the same solvent, usually an aromatic solvent such as xylene. An elevated temperature is required for the Claisen rearrangement to occur, and an acid catalyst is utilized in the second stage to effect cyclization.

European Patent Application No. 92,102 published Oct. 10, 1983 and U.S. Pat. No. 4,321,204 disclose single solvent systems for all three stages of the process, thus providing the benefit of avoiding costly isolation of 2-methallyloxyphenol and introduction of a second solvent. However, in EPA No. 92,102, an expensive quaternary phase transfer catalyst is required in the etherification step and the catalyst, because of its cost, must be separated for reuse before proceeding to the second and third stages. In U.S. Pat. No. 4,321,204 the single solvent is a polyhydroxy alkyl ether, requiring pressurization during the Claisen rearrangement.

SUMMARY OF THE INVENTION

It has now been found that by employing, in the preparation of 2-methallyloxyphenol by the reaction of methallyl chloride with catechol, a reaction medium comprising an inert aromatic hydrocarbon solvent and an amine capable of quaternization with methallyl chloride, the separate addition of a phase transfer catalyst to the reaction mixture is not required and the solvent can be carried through the subsequent rearrangement and cyclization stages to form the benzofuranyl intermediate for production of carbofuran. Thus, the cumbersome and time-consuming isolation of 2-methallyloxyphenol after etherification and the subsequent introduction of a different solvent of prior processes are avoided. Simultaneously, high selectivity to the desired 2-methallyloxyphenol (low dietherification and ring alkylation) and high catechol conversion at rapid reaction rate are achieved, thereby avoiding costly separation and recycle of catechol and other inefficiencies of prior processes.

DETAILED DESCRIPTION

In the process of the invention, methallyl chloride is reacted with an alkali metal catecholate formed from catechol and a basic alkali metal compound such as an alkali metal carbonate, bicarbonate or any mixture thereof. The catecholate may be preformed but it is preferably formed in situ by reacting catechol and methallyl chloride in the presence of the alkali metal base. The mole ratio of catechol (or catecholate) to methallyl chloride may range from about 1:2 to about 1:1.2. The molar excess of methallyl chloride should be sufficient for quaternization with the amine in the reaction mixture. The mole ratio of catechol to the basic alkali metal compound will be from about 2:1 to about 1:1.8.

Suitable aromatic hydrocarbon solvents for use in the process of the invention are liquids under room temperature conditions and include any of the xylenes and mixed xylenes, tetralin, benzene, toluene, ethylbenzene, and any mixtures thereof. The aromatic hydrocarbon solvent is used in large excess with respect to the reactants and in an amount effective to provide a fluid reaction mass. A proportion of about 300 parts by volume of hydrocarbon solvent per 100-150 parts by volume of catechol and methallyl chloride combined is effective, but other proportions are also useful.

Suitable amines are any monoamines which are liquid at room temperature. The amines must also be miscible with the aromatic hydrocarbon solvent and quaternize with methallyl chloride to form a phase transfer catalyst in situ. Representative amines include trialkyl ($C_2$-$C_8$) amines, such as triethylamine, triisopropylamine and tri-n-butylamine, N-heterocyclic amines such as pyridine and quinoline, and any mixtures of the amines. The amine should be present in an amount effective to react with excess methallyl chloride to form sufficient amounts of quaternary salt to catalyze the etherification reaction. The mole ratio of catechol to amine may range from about 10:1 to 1:1.

In one mode of operation, a reactor is charged with catechol, the alkali metal base, the amine, sodium dithionite (reducing agent), and the aromatic hydrocarbon solvent. During the charging operation as well as during the reaction an inert atmosphere is maintained in the reactor. Methallyl chloride addition may begin either with the initial application of heat to the reaction mixture or at a later time when the reaction mixture is at an elevated temperature. The rate of methallyl chloride addition may vary widely, but should not be so fast as to cause too rapid an evolution of carbon dioxide from the alkali metal carbonate or bicarbonate. The metered addition of methallyl chloride allows a higher reflux temperature (125°-135° C.) to be reached, although maximum temperatures during the reaction may be as low as 80° C. Lower temperatures, of course, usually require longer reaction times. Normal reaction times are 2 to 6 hours during which the reaction mixture is agitated, but reaction time may be as long as 24 hours or more. Upon completion of reaction, the reaction mass is cooled, neutralized with a mineral acid or other acidic solution, the aqueous and organic phases are separated, and the hydrocarbon phase containing the 2-methallyloxyphenol is dried. This hydrocarbon phase may then be utilized directly in the Claisen rearrangement and the subsequent cyclization to produce the desired 2,3-dihydro-2,2-dimethyl-7-hydroxybenzofuran in accordance with known procedures.

In another mode of operation, catechol, the amine, the alkali metal base, sodium dithionite, the aromatic hydrocarbon solvent, and methallyl chloride are placed in a reactor under an inert atmosphere and then heated to a temperature in the range specified above. In this method of operation, selection of the solvent is important since catechol may react too rapidly with the alkali metal base, causing uncontrollable evolution of carbon dioxide. Selection of a solvent, e.g., tetralin, in which catechol is sparingly soluble avoids this rapid evolution of carbon dioxide and the attendant process problems. Isolation of the product may be similar to the first mode of operation, although filtration of the reaction mixture may precede a separation of two phases, one of which is composed primarily of aromatic hydrocarbon solvent and 2-methallyloxyphenol and the other composed of the amine, some 2-methallyloxyphenol, unreacted catechol, and by-products.

Alternatively, the quaternary salt can be prepared separately and then utilized in the etherification reaction. For example, the amine, mehallyl chloride, and the aromatic hydrocarbon solvent can be mixed in the reactor for a period of time sufficient for formation of the quaternary salt. Following the introduction of the alkali metal base and sodium dithionite, this mixture is heated to the reaction temperature and molten catechol is fed incrementally or continuously into the reaction mixture. Another variation in which the quaternary salt is preformed involves mixing the amine and methallyl chloride and feeding this mixture into a heated reactor containing catechol, the alkali metal base, the solvent, and sodium dithionite.

Regardless of the mode of action utilized, the etherification may be run at atmospheric pressure or in a closed reactor under autogenous pressure. Reaction time can vary considerably, depending on the specific aromatic hydrocarbon solvent utilized, the temperature, and the pressure. Preferred reaction times are between 2 and 6 hours. In all cases a solution of 2-methallyloxyphenol in aromatic hydrocarbon solvent is obtained which can be used in the Claisen rearrangement and ring closure steps.

The process is effective for producing 2-methallyloxyphenol in over 60% yield at about 80% selectivity to usable products and about 80% conversion of catechol, while also permitting entry into the second and third stages for production of 2,3-dihydro-2,3-dimethyl-7-hydroxy benzofuran without solvent exchange. If a suitable catalyst is present in the reaction mixture, e.g., aluminum chloride, aluminum isopropoxide or magnesium chloride, the Claisen rearrangement and ring closure can proceed simultaneously with etherification.

The following examples further illustrate the invention but are not intended to limit the scope thereof. In the examples and throughout this specification and in the claims, all parts and percentages are by weight and temperatures are °C. unless otherwise indicated.

EXAMPLE 1

Catechol (55 g, 0.5 mole), sodium carbonate (35 g, 0.33 mole), triethylamine (10 g, 0.1 mole), and xylene (300 ml) were placed in a 1 liter, three-necked flask with 0.1 g sodium dithionate as a reducing agent. The reaction flask was fitted with a nitrogen inlet, thermometer, a Dean-Stark trap and a reflux condenser topped with a dry-ice acetone trap. The reactants were stirred, heated, and methallyl chloride (62 g, 0.68 mole) was introduced by a syringe pump at a rate of 0.8 cc per minute during a 105 minute period. The temperature of the reaction mixture was maintained at 132° C. After the methallyl chloride addition was complete, the temperature was maintained for an additional fifteen minutes, and then the reactor allowed to cool to 40° C. Upon cooling, 300 ml of 10% aqueous HCl was added with stirring to neutralize the excess sodium carbonate and to dissolve any triethylamine quaternary salts. The organic/aqueous layers were separated, and the xylene layer was filtered through coalescent paper to remove entrained water. The aqueous layer was extracted twice with 250 ml of ethyl acetate to remove unreacted catechol. The xylene layer and the combined ethyl acetate extract were each weighed and analyzed by gas chromatography. The combined yield of 2-methallyloxyphenol plus combined yield of 2-methallyloxyphenol plus 3-methallylcatechol, the desired product of the Claisen rearrangement, was 51.5 g, a yield of 62.7% based on catechol charged. The material balance accounted for 95.7% of the catechol charged and showed that 77.8% of it had been converted to products and by-products. The conversion to usable products, i.e., selectivity, was 80.6%.

EXAMPLE 2

Catechol (55 g, 0.5 mole) was placed in a 1 liter, three-necked flask fitted with a nitrogen inlet, reflux condenser and thermometer. To the catechol was added sodium carbonate (53 g, 0.5 mole) and tetralin (341 g, 2.6 moles). The mixture was stirred for 15 minutes at room temperature without noticeable catechol dissolution. Methallyl chloride (81.7 g, 0.9 mole) was added to the mixture which was then stirred for approximately 15 minutes. There was still no noticeable catechol dissolution. To the mixture was added tributylamine (93 g, 0.5 mole), which caused a temperature rise to 30° C. The reaction medium was then heated to 120° C., causing carbon dioxide evolution. The reaction was stirred and heated for a total of 6 hours and then cooled. The precipitated salts were filtered leaving 448.2 g of homogeneous liquid. An analysis indicated 88.3% catechol accountability, 93.2% catechol conversion, and 69.6% selectivity to 2-methallyloxyphenol. The yield of 2-methallyloxyphenol was 64.9% based on catechol charged.

EXAMPLE 3

This example illustrates the effect of a lower reaction temperature.

Catechol (55 g, 0.5 mole), sodium carbonate (27 g, 0.26 mole), methallyl chloride (81 g, 0.9 mole), tributylamine (92.5 g, 0.5 mole), and tetralin (360 g, 2.7 moles) were placed in a 1 liter, three-necked flask, fitted with a reflux condenser, thermometer and nitrogen inlet. The reaction mixture was heated to 80° C. and held for 20 hours. Slight evolution of carbon dioxide was noted. After cooling to 30° C. and filtering and washing the resultant salts, 599 g of liquid was transferred into a separatory funnel where it separated into two distinct layers. The upper layer (435 g) was found to contain 35.4 g 2-methallyloxyphenol, 2.6 g catechol, and 10.2 g of by-products. The lower layer was found to contain 18.9 g 2-methallyloxyphenol, 6.4 g catechol and about 2.0 g of by-products. Accountability was 93.8% of catechol charged with 83.8% conversion and 79% selectivity to 2-methallyloxyphenol. The overall yield of 2methallyloxyphenol based on catechol charged was 66.2%.

EXAMPLE 4

This example illustrates the effect of preforming a quaternary salt.

Catechol (55 g, 0.5 mole) was placed in a dropping funnel under nitrogen and heated until molten (105° C.). Separately, a solution of triethylamine (56 g, 0.5 mole) and methallyl chloride (68 g, 0.75 mole) in 300 ml xylene was mixed for 24 hours to form the quaternary salt. This salt solution was then heated to reflux (120° C.) in the presence of $Na_2CO_3$ (35 g, 0.33 mole). After one hour of heating, the molten catechol was fed intermittently into the hot quaternary salt solution during a period of about two hours. The reaction mixture was allowed to cool after the addition and then was washed with 300 ml of 20% aqueous HCl. Extraction of the aqueous phase and analysis of the extract and the xylene phase was done as described in Example 1. Analysis indicated that the combined yield of 2-methallyloxyphenol and 3-methallylcatechol was 52.6% at 81.4% selectivity and 64.6% catechol conversion.

EXAMPLE 5

This example illustrates another method of utilizing preformed quaternary salt.

Catechol (55 g, 0.5 mole), sodium bicarbonate (75 g, 0.89 mole), and tetralin (300 ml) were placed in a 1 liter, three-necked flask fitted with a nitrogen inlet, reflux condenser, and thermometer. This mixture was heated at 95° C. for one hour with stirring. A previously prepared mixture of tributylamine (9.25 g, 0.05 mole) and methallyl chloride (81 g, 0.89 mole) was then added in one portion. The reaction mixture was heated at 95° C. with stirring for five additional hours. After cooling, the reaction mixture was filtered, and the collected solids were washed with tetralin (30 ml). The filtrate was homogeneous and was analyzed by gas chromatography. This analysis indicated a 59.2% yield of 2-methallyloxyphenol and 3-methallylcatechol combined. The selectivity was 76.2%, and conversion of catechol was 77.6%.

We claim:

1. In a process for preparing the 2-methallyloxyphenol precursor to 2,3-dihydro-2,2-dimethyl-7-hydroxybenzofuran by the reaction of methallyl chloride, catechol and a basic alkali metal compound to form a catecholate, wherein said precursor and hydroxybenzofuran are formed in the same solvent medium, the improvement which comprises employing an aromatic hydrocarbon as the solvent, the medium also containing an amine capable of reacting in situ with methallyl chloride to form a quaternary catalyst.

2. The process of claim 1 wherein the catecholate is formed in situ by the reaction of catechol and a basic alkali metal compound.

3. The process of claim 2 wherein the amount of the amine is effective to form the quaternary catalyst.

4. The process of claim 2 wherein the alkali metal compound is an alkali metal carbonate or bicarbonate.

5. The process of claim 2 wherein the alkali metal compound is sodium carbonate or sodium bicarbonate.

6. The process of claim 1 wherein the aromatic hydrocarbon solvent is selected from tetralin, xylene, benzene, toluene, ethylbenzene and any mixture thereof.

7. The process of claim 1 wherein the amine is a liquid trialkylamine.

8. The process of claim 7 wherein the trialkylamine is triethylamine or tri-n-butylamine.

9. The process of claim 1 wherein the hydrocarbon solvent is tetralin and the amine is tri-n-butylamine.

10. The process of claim 1 wherein the hydrocarbon solvent is xylene and the amine is triethylamine.

11. The process of claim 1 wherein the mole ratio of the catecholate to the trialkylamine is about 10:1 to 1:1.

* * * * *